(12) United States Patent
Spazier

(10) Patent No.: US 12,263,721 B2
(45) Date of Patent: Apr. 1, 2025

(54) DEVICE FOR IMPROVING INTERIOR AIR QUALITY IN A VEHICLE AND A VEHICLE

(71) Applicant: MERCEDES-BENZ GROUP AG, Stuttgart (DE)

(72) Inventor: Norbert Spazier, Bondorf (DE)

(73) Assignee: MERCEDES-BENZ GROUP AG, Stuttgart (DE)

( * ) Notice: Subject to any disclaimer, the term of this patent is extended or adjusted under 35 U.S.C. 154(b) by 353 days.

(21) Appl. No.: 17/773,214

(22) PCT Filed: Oct. 27, 2020

(86) PCT No.: PCT/EP2020/080119
§ 371 (c)(1),
(2) Date: Apr. 29, 2022

(87) PCT Pub. No.: WO2021/083859
PCT Pub. Date: May 6, 2021

(65) Prior Publication Data
US 2022/0379688 A1 Dec. 1, 2022

(30) Foreign Application Priority Data
Oct. 30, 2019 (DE) ............... 10 2019 007 536.6

(51) Int. Cl.
*B60H 3/00* (2006.01)
*A61L 9/20* (2006.01)

(52) U.S. Cl.
CPC ............ *B60H 3/0078* (2013.01); *A61L 9/20* (2013.01); *A61L 2209/11* (2013.01); *A61L 2209/12* (2013.01); *A61L 2209/16* (2013.01)

(58) Field of Classification Search
CPC ...... B60H 3/0078; A61L 9/20; A61L 2209/11; A61L 2209/12; A61L 2209/16; A61L 2209/14; F24F 8/22
See application file for complete search history.

(56) References Cited

U.S. PATENT DOCUMENTS

| 5,933,702 A | 8/1999 | Goswami |
| 9,963,017 B2 | 5/2018 | Kim et al. |

(Continued)

FOREIGN PATENT DOCUMENTS

| CN | 1198679 A | 11/1998 |
| CN | 202209742 U | 5/2012 |

(Continued)

OTHER PUBLICATIONS

International Search Report mailed Feb. 8, 2021 in related/corresponding International Application No. PCT/EP2020/080119.

(Continued)

*Primary Examiner* — David E Smith
*Assistant Examiner* — Christopher J Gassen
(74) *Attorney, Agent, or Firm* — PATENT PORTFOLIO BUILDERS PLLC

(57) ABSTRACT

A device for improving an interior air quality in a vehicle includes a photoreactor and a control device. The photoreactor is connectable, by a photoreactor line section, between a fresh air intake and an air distribution system of a ventilation system and/or air conditioning system of the vehicle. The photoreactor line section has a controllable valve in each of the two end regions, i.e., at the respective points at which it is connectable on the one hand to the fresh air intake and on the other hand to the air distribution system. The photoreactor has UV-C LEDs that emit UV-C radiation. The control device controls the air passing through the photoreactor using the controllable valves arranged in the photoreactor line section in such a way that the air passing through is exposed to a predetermined UV-C radiation dose.

17 Claims, 1 Drawing Sheet

(56) References Cited

U.S. PATENT DOCUMENTS

Figure 1:
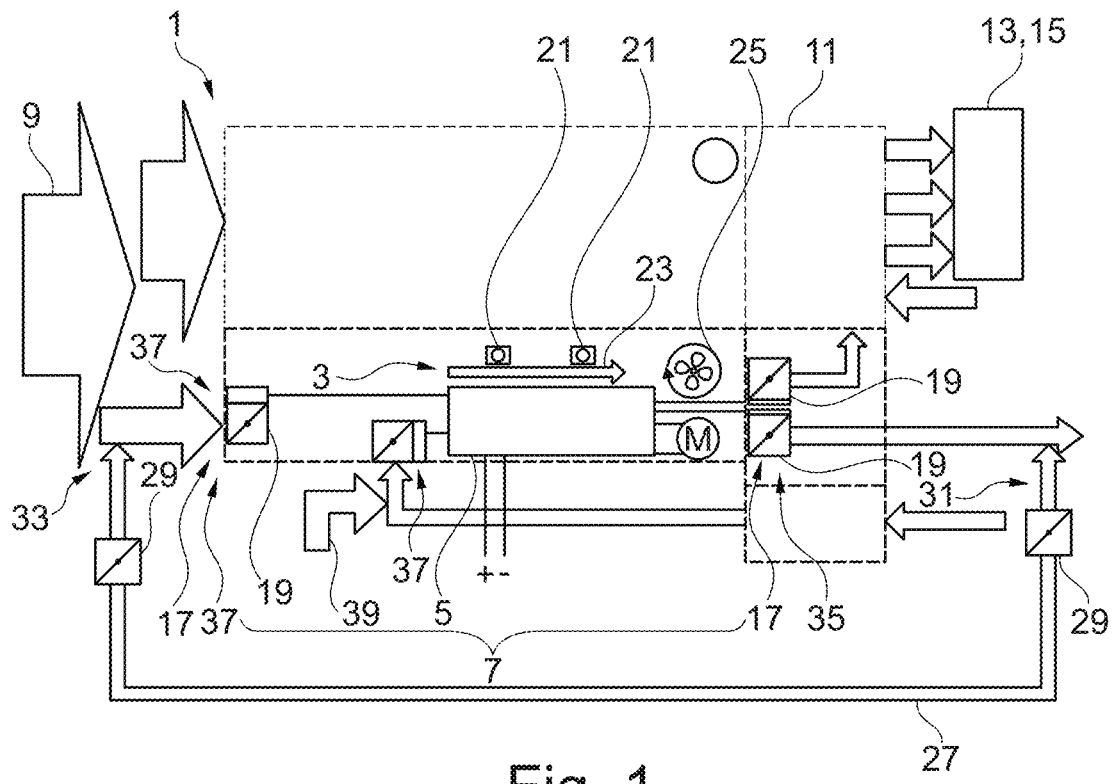

| | | |
|---|---|---|
| 2009/0098014 A1 | 4/2009 | Longstaff |
| 2009/0217690 A1* | 9/2009 | Silderhuis ............... F24F 8/192 |
| | | 62/264 |
| 2017/0354928 A1 | 12/2017 | Michniewicz et al. |

FOREIGN PATENT DOCUMENTS

| | | |
|---|---|---|
| CN | 104654473 A | 5/2015 |
| DE | 3637702 A1 | 5/1988 |
| DE | 10346826 A1 | 4/2005 |
| DE | 202006017471 U | 2/2007 |
| DE | 112015000091 T5 | 3/2016 |
| DK | 179808 B1 | 7/2019 |
| WO | 2019166545 A1 | 9/2019 |

OTHER PUBLICATIONS

Office Action created Jun. 30, 2020 in related/corresponding DE Application No. 10 2019 007 536.6.
Written Opinion mailed Feb. 8, 2021 in related/corresponding International Application No. PCT/EP2020/080119.
Office Action dated Mar. 23, 2024 in related/corresponding CN Application No. 2020800748497.
Office Action dated Nov. 6, 2024 in related/corresponding CN Application No. 202080074849.
Office Action dated Jan. 17, 2025 in related/corresponding CN Application No. 202080074849.

* cited by examiner

DEVICE FOR IMPROVING INTERIOR AIR QUALITY IN A VEHICLE AND A VEHICLE

BACKGROUND AND SUMMARY OF THE INVENTION

Exemplary embodiments of the invention relate to a device for improving interior air quality in a vehicle and a vehicle.

It is known to deactivate pathogenic germs, such as viruses, bacteria, and fungi, present in the air using high-energy radiation for the disinfection and cleaning of ventilation systems and air-conditioning systems. In particular, this means destroying them or at least damaging them in such a way that they no longer have a pathogenic effect. In other words, it is imperative that a correspondingly high radiation power and/or radiation dose be provided, such that a correspondingly deactivating effect on the pathogenic germs can be brought about. For this purpose, values and/or orders of magnitude for the air quantity or an air flow and the radiation powers required for this are known.

Furthermore, it is known to effect this deactivation of the pathogenic germs using UV-C radiation and corresponding sufficiently high radiation power. In terms of system technology, however, it is necessary to work on the one hand with the already mentioned high radiation power, but on the other hand also with a small distance to an active surface. The necessary prerequisites for systems for air purification are regularly only given in the architectural sector, such as medical practices, hospitals, and/or the food processing industry.

In particular, the appropriate necessary space or volumes are available in the architectural sector, in contrast to the automotive sector. In addition, radiation sources—such as high-voltage radiation sources—can be used in the architectural sector, which would lead to a large effort and/or high costs when used in the automotive field, which is why they are only used in special applications which are, for example, relevant to safety, such as, in particular, in a vehicle's driving light.

A filter system for a motor vehicle is known from the German application document DE 10346826 A1, having at least one electric filter, one photo reactor and one plasma reactor each, which are arranged in an air duct, wherein the electric filter is arranged in front of the photo reactor and the plasma reactor. However, this does not solve the problems addressed here, in particular the problem of achieving a correspondingly high deactivating radiation power in a small space—which is available in vehicles—if only UV-C radiation is to be used.

Exemplary embodiments of the invention are directed to a device for improving interior air quality in a vehicle and a vehicle, wherein the disadvantages mentioned do not occur. In particular, in which UV-C radiation can be used in a simple manner to deactivate pathogenic germs.

According to embodiments, there is a device for improving the interior air quality in a vehicle, having a photoreactor and a control device, wherein the photoreactor can be arranged, in particular connected, by means of a photoreactor line section between a fresh air intake and an air distribution system of a ventilation system and/or air conditioning system of the vehicle, wherein the photoreactor line section has a controllable valve in both end regions, i.e., at the respective points at which it can be connected on the one hand to the fresh air intake and on the other hand to the air distribution system, wherein the photoreactor has UV-C LEDs which are set up to emit UV-C radiation, wherein the control device is set up to control the air passing through the photoreactor by means of the controllable valves arranged in the photoreactor line section in such a way that the air passing through is exposed to a predeterminable dose of UV-C radiation. This refers in particular to the fact that an input volume flow—controlled by the valve that can be controlled on the input side—is controlled in such a way that the air flowing through has a correspondingly sufficient dwelling time within the photoreactor. Furthermore, it is preferably provided that the control device also controls the valve that can be controlled on the outlet side in such a way that the air flowing through has a correspondingly sufficient dwelling time within the photoreactor. This makes it possible, in particular, to expose pathogenic germs in the air of the ventilation system and/or air conditioning system of the vehicle to UV-C radiation that can be emitted in vehicles by means of UV-C LEDs, in particular by means of a prolonged dwelling time under the influence of the UV-C radiation, in such a way that the germs are safely deactivated. In particular, it is necessary for this that the control device be set up to control an air flow to the photoreactor by means of the controllable valves in such a way that a corresponding radiation dose can be effected on the air present in the photoreactor. In this case, it is also possible to adjust a fresh air supply by means of the fresh air intake in such a way that a correspondingly sufficient radiation dose is applied depending on a pathogenic germ load. In particular, it is possible to compensate for or at least significantly improve the disadvantage of the smaller available space and the limited choice of radiation sources. In other words—in comparison to the volumes and radiation sources available in the architectural field—for radiation sources and volumes available in the automotive field to have a sufficiently deactivating effect on the pathogenic germs, which are present in the air.

According to a development of the invention, the photoreactor line section is designed as a bypass to a connection between the fresh air intake and the air distribution system. This has the particular advantage that a volume flow in the photoreactor can be adjusted in a particularly flexible manner, since, in relation to a fresh air intake, only a part of the fresh air drawn in must also be passed through the photoreactor.

Furthermore, it is preferably provided that an outlet of the photoreactor is connectable to nozzles in an interior of the vehicle, preferably directly, wherein the nozzles in the interior of the vehicle are preferably staged, in particular optically and/or acoustically.

According to a development of the invention, it is provided that a filter device, in particular an air filter device, preferably an HEPA filter, is connected upstream of the device and/or the photoreactor. This has the particular advantage that microscopic and/or macroscopic particles in the fresh air drawn in can be effectively removed in a simple manner.

According to a development of the invention, it is provided that the photoreactor has an air-moving device, in particular a fan, which is set up to mix the air in the photoreactor, i.e., which is contained in the photoreactor. This has the particular advantage that the air present in the photoreactor can be brought into contact with the UV-C radiation of the UV-C LEDs in a particularly effective manner.

According to a development of the invention, the photoreactor has a return bypass with preferably two controllable valves arranged at the ends, i.e., at the beginning of the return bypass and at the end of the return bypass, wherein the return bypass is set up to connect an outlet of the photoreactor to an inlet of the photoreactor, and wherein the control device is preferably additionally set up to guide the air flowing through the photoreactor from the outlet back to the inlet of the photoreactor by means of the controllable valves arranged in the return bypass in such a way that the air is preferably completely germ-free. Particularly preferably, it is provided that the air is at least 98%, preferably 99%, particularly preferably 99.9% germ-free, preferably relative to a volume proportion of the germs in the total air mass. This has the particular advantage that, by repeatedly passing the air through the photoreactor, air which is particularly contaminated with germs can be repeatedly exposed to UV-C radiation without the air with a considerable germ contamination being fed to the air distribution system and thus to the interior of the vehicle.

According to a development of the invention, an input of the photoreactor can be connected to circulating air, in particular a circulating air output, of the ventilation system and/or the air conditioning system of the vehicle. This has the particular advantage that germs that are introduced into the air in the interior of the vehicle can also be efficiently deactivated. By way of example, in the case of a passenger, who has a cold and/or is ill and has to sneeze, such an entry of pathogenic germs into the interior air of the vehicle occurs. By means of the function of the circulating air, whereby air of the interior of the vehicle can again be passed through the ventilation system and/or air conditioning system and thus also through the photoreactor, it is possible to efficiently irradiate, in particular treat, the interior air with UV-C radiation. As a result, pathogenic germs present in the air can be deactivated.

According to a further development of the invention, it is provided that the device, in particular the photoreactor and/or components of the device, such as chambers and/or air baffles, is made of a metal, preferably stainless steel, particularly preferably X5CrNi18-10, or has a metal, preferably stainless steel, particularly preferably X5CrNi18-10. This has the particular advantage that a particularly durable device can be obtained.

According to a development of the invention, the photoreactor has a meandering structure in which the UV-C LEDs, which the photoreactor has, are preferably homogeneously distributed and arranged in such a way that air, which is guided through the meandering structure of the photoreactor, is intensively and in particular effectively contacted with the UV-C radiation. This has the advantage in particular that the particularly effective contacting of the air with the UV-C radiation can in particular also reduce an energy requirement for the UV-C radiation to a minimum, such that as a result, fuel and/or electricity can be saved in a vehicle during operation of the vehicle.

Furthermore, it is preferably provided that the control device is operatively connected to the controllable valves.

Exemplary embodiments are also directed to a vehicle comprising a device according to the invention or a device according to one of the embodiments mentioned above. In connection with the vehicle, the advantages already explained in connection with the device are realized in particular.

BRIEF DESCRIPTION OF THE DRAWING FIGURES

Figure 2:
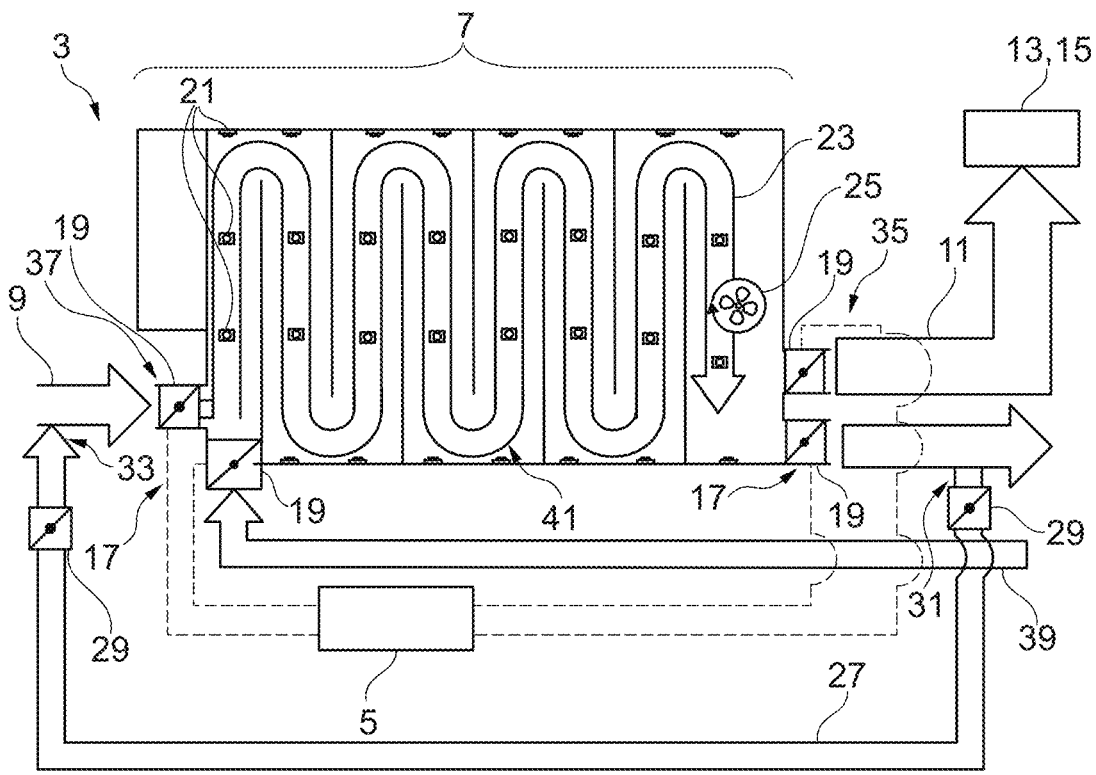

The invention is explained in more detail below with reference to the drawings. Here are shown:

FIG. 1 a schematic depiction of an exemplary embodiment of the device,

FIG. 2 a schematic depiction of an exemplary embodiment of the photoreactor.

DETAILED DESCRIPTION

FIG. 1 shows a schematic representation of an embodiment of the device 1 for improving interior air quality in a vehicle, having a photoreactor 3 and a control device 5, wherein the photoreactor 3 can be arranged, in particular connected, by means of a photoreactor line section 7, between a fresh air intake 9 and an air distribution system 11 of a ventilation system 13 and/or air conditioning system 15 of the vehicle. The photoreactor line section has a controllable valve 19 in both end regions 17, i.e., at the respective points at which it can be connected to the fresh air intake 9 on the one hand and to the air distribution system 11 on the other hand. The photoreactor 3 has UV-C LEDs 21, which are set up to emit UV-C radiation. The control device 5 is set up to control the air 23 passing through the photoreactor 3 by means of the controllable valves 19 arranged in the photoreactor line section 7 in such a way that the air 23 passing through is exposed to a predeterminable dose of UV-C radiation. This refers in particular to the fact that an input volume flow—controlled by the controllable valve 19 on the input side—is controlled in such a way that the air 23 flowing through has a correspondingly sufficient dwelling time within the photoreactor 3.

The photoreactor line section 7 is preferably designed as a bypass to a connection between the fresh air intake 9 and the air distribution system 11.

Furthermore, it is preferably provided that a filter device (not shown in the figures), in particular an air filter device, preferably a HEPA filter, is connected upstream of the device 1 and/or the photoreactor 3.

The photoreactor 3 preferably has an air-moving device 25, in particular a fan, which is set up to mix the air 23 in the photoreactor 3.

The photoreactor 3 preferably has a return bypass 27 (shown in FIG. 2) having preferably two controllable valves 29 arranged at the ends, i.e., at the beginning 31 of the return bypass 27 and at the end 33 of the return bypass 27. The return bypass 27 is set up to connect an outlet 35 of the photoreactor 3 to an inlet 37 of the photoreactor 3. The control device 5 is preferably additionally set up, by means of the controllable valves 29 arranged in the return bypass 27, to guide the air 23 flowing through the photoreactor 3 from the outlet 35 back to the inlet 37 of the photoreactor 3 in such a way that the air 23 is preferably completely germ-free. Particularly preferably, the air is at least 98%, preferably 99%, particularly preferably 99.9% germ-free, preferably relative to a volume proportion of the germs in the total air volume or relative to a mass proportion of the germs in the total air mass.

Furthermore, it is preferably provided that an inlet 37 of the photoreactor 3 can be connected to circulating air, in particular a circulating air outlet 39, of the ventilation system 13 and/or the air conditioning system 15 of the vehicle.

Furthermore, it is preferably provided that the device 1, in particular the photoreactor 3 and/or components of the device 1, such as chambers and/or air baffles, is made of a metal, preferably stainless steel, particularly preferably X5CrNi18-10, or has a metal, preferably stainless steel, particularly preferably X5CrNi18-10.

In FIG. 1 as well as in FIG. 2, identical and/or functionally identical parts are provided with the same reference numerals, which is why reference is made to the above description of the figures accordingly.

FIG. 2 shows a schematic depiction of an exemplary embodiment of the photoreactor 3.

FIG. 2 shows that the photoreactor 3 has a meandering structure 41 in which the UV-C LEDs 21, which the photoreactor 3 has, are preferably homogeneously distributed and arranged in such a way that air 23, which is guided through the meandering structure of the photoreactor 3, is intensively and, in particular, effectively contacted with the UV-C radiation.

In FIG. 2, only some of the UV-C LEDs 21 shown are provided with a corresponding reference numeral 21, in particular in order not to impair clarity.

The meandering structure 41 has been omitted in FIG. 1—for reasons of clarity—but the meandering structure 41 can be seen in FIG. 2.

Although the invention has been illustrated and described in detail by way of preferred embodiments, the invention is not limited by the examples disclosed, and other variations can be derived from these by the person skilled in the art without leaving the scope of the invention. It is therefore clear that there is a plurality of possible variations. It is also clear that embodiments stated by way of example are only really examples that are not to be seen as limiting the scope, application possibilities or configuration of the invention in any way. In fact, the preceding description and the description of the figures enable the person skilled in the art to implement the exemplary embodiments in concrete manner, wherein, with the knowledge of the disclosed inventive concept, the person skilled in the art is able to undertake various changes, for example, with regard to the functioning or arrangement of individual elements stated in an exemplary embodiment without leaving the scope of the invention, which is defined by the claims and their legal equivalents, such as further explanations in the description.

The invention claimed is:

1. A device for improving interior air quality in a vehicle, the device comprising:
   a photoreactor having UV-CLEDs configured to emit UV-C radiation;
   a photoreactor line section having first and second end regions; and
   a control device coupled to the photoreactor,
   wherein the photoreactor is connected, via the photoreactor line section between a fresh air intake and an air distribution system of a ventilation system or between the fresh air intake and an air conditioning system of the vehicle,
   wherein the photoreactor line section has a first controllable valve in the first end region configured to connect the photoreactor line section to the fresh air intake and a second controllable valve in the second end region configured to connect the photoreactor line section to the air distribution system,
   wherein the control device is configured to control air passing through the photoreactor by controlling the controllable valves arranged in the photoreactor line section in such a way that the air passing through is exposed to a predetermined UV-C radiation dose,
   wherein the photoreactor has a return bypass with a third controllable valve arranged at a first end of the photoreactor and coupled to an inlet of the photoreactor upstream of the first controllable valve so that air flowing through the third controllable valve is supplied to the first controllable valve,
   wherein the return bypass has a fourth controllable valve arranged at a second end of the photoreactor and coupled to an outlet of the photoreactor downstream of the second controllable valve so that air passing through second controllable valve is supplied to the fourth controllable valve, and
   wherein, when the first, second, third, and fourth controllable valves are open, air from the fresh air intake passes, in stated order, through the first controllable valve, by the photoreactor, the second controllable valve, the fourth controllable valve, and then the third controllable valve.

2. The device of claim 1, wherein the photoreactor line section is configured as a bypass to a connection between the fresh air intake and the air distribution system.

3. The device of claim 1, wherein a HEPA filter is connected upstream of the device or of the photoreactor.

4. The device of claim 1, wherein the photoreactor has a fan arranged to mix the air in the photoreactor.

5. The device of claim 1, wherein the inlet of the photoreactor is configured to be connected to a circulating air outlet of the ventilation system or of the air conditioning system.

6. The device of claim 1, wherein the photoreactor or components of the device is/are made of stainless steel or has/have stainless steel.

7. The device of claim 1, wherein the photoreactor has a meandering structure in which the UV-C LEDs are homogeneously distributed and arranged in such a way that air guided through the meandering structure of the photoreactor is effectively contacted with the UV-C radiation.

8. A vehicle, comprising:
   a fresh air intake;
   a ventilation system having an air distribution system;
   an air conditioning system;
   a connection between the fresh air intake and the air distribution system; and
   a device for improving interior air quality in the vehicle, the device comprising
      a photoreactor having UV-CLEDs configured to emit UV-C radiation;
      a photoreactor line section having first and second end regions; and
      a control device coupled to the photoreactor,
      wherein the photoreactor is connected, via the photoreactor line section between the fresh air intake and the air distribution system of a ventilation system or between the fresh air intake and an air conditioning system of the vehicle,
      wherein the photoreactor line section has a first controllable valve in the first end region configured to connect the photoreactor line section to the fresh air intake and a second controllable valve in the second end region configured to connect the photoreactor line section to the air distribution system,
      wherein the control device is configured to control air passing through the photoreactor by controlling the controllable valves arranged in the photoreactor line section in such a way that the air passing through is exposed to a predetermined UV-C radiation dose,
      wherein the photoreactor has a return bypass with a third controllable valve arranged at a first end of the photoreactor and coupled to an inlet of the photoreactor upstream of the first controllable valve so that air flowing through the third controllable valve is supplied to the first controllable valve, wherein the return bypass has a fourth controllable valve arranged at a second end of the photoreactor and coupled to an outlet of the photoreactor downstream of the second controllable valve so that air passing through second controllable valve is supplied to the fourth controllable valve, and wherein, when the first, second, third, and fourth controllable valves are open, air from the fresh air intake passes, in stated order, through the first controllable valve, by the photoreactor, the second controllable valve, the fourth controllable valve, and then the third controllable valve.

9. The vehicle of claim 8, further comprising:
a HEPA filter is connected upstream of the device or of the photoreactor.

10. The vehicle of claim 8, wherein the photoreactor has a fan arranged to mix the air in the photoreactor.

11. The vehicle of claim 8, wherein the inlet of the photoreactor is configured to be connected to a circulating air outlet of the ventilation system or of the air conditioning system.

12. The vehicle of claim 8, wherein the photoreactor or components of the device is/are made of stainless steel or has/have stainless steel.

13. A device for improving interior air quality in a vehicle, the device comprising:
a photoreactor line section having a first controllable valve in a first end region of the photoreactor line section and a second controllable valve in a second end region of the photoreactor line section, wherein the first controllable valve is couplable with a fresh air intake of the vehicle and the second controllable valve is couplable with at least an air distribution system of the vehicle, a photoreactor having UV-CLEDs configured to emit UV-C radiation and arranged to receive air from the fresh air intake via the first controllable valve and to supply the air, after being exposed to the UV-C radiation, to the air distribution system; and a return bypass with a third controllable valve arranged at a first end of the return bypass and coupled to the first controllable valve so that air flowing through the third controllable valve is supplied to the first controllable valve, wherein the return bypass has a fourth controllable valve arranged at a second end of the return bypass and coupled to the fourth controllable valve so that air passing through second controllable valve is supplied to the fourth controllable valve without being fed to the air distribution system, and wherein, when the first, second, third, and fourth controllable valves are open, air from the fresh intake passes, in stated order, through the first controllable valve, by the photoreactor, the second controllable valve, the fourth controllable valve, and then the third controllable valve.

14. The device of claim 13, wherein the photoreactor line section is configured as a bypass to a connection between the fresh air intake and the air distribution system.

15. The device of claim 13, wherein the photoreactor has a fan arranged to mix the air in the photoreactor.

16. The device of claim 13, wherein an inlet of the photoreactor is configured to be connected to a circulating air outlet of a ventilation system of the vehicle or of an air conditioning system of the vehicle.

17. The device of claim 13, wherein the photoreactor has a meandering structure in which the UV-C LEDs are homogeneously distributed and arranged in such a way that air guided through the meandering structure of the photoreactor is effectively contacted with the UV-C radiation, wherein the meandering structure is configured so that the air passes through the photoreactor line section initially in a first direction, then in a second direction, and then in a third direction, wherein the first and third directions are a same direction and the second direction is an opposite direction of the first and third directions.

* * * * *